(12) United States Patent
Jalkanen (10) Patent No.: US 7,534,423 B2
(45) Date of Patent: May 19, 2009

(54) METHOD FOR INDUCING AN ELEVATED LEVEL OF ADENOSINE IN AN INDIVIDUAL

(75) Inventor: Sirpa Jalkanen, Piispanristi (FI)

(73) Assignee: Faron Pharmaceuticals Oy, Turku (FI)

( * ) Notice: Subject to any disclaimer, the term of this patent is extended or adjusted under 35 U.S.C. 154(b) by 256 days.

(21) Appl. No.: 10/546,653

(22) PCT Filed: Mar. 19, 2004

(86) PCT No.: PCT/FI2004/000158

§ 371 (c)(1),
(2), (4) Date: Aug. 24, 2005

(87) PCT Pub. No.: WO2004/084933

PCT Pub. Date: Oct. 7, 2004

(65) Prior Publication Data

US 2006/0198821 A1 Sep. 7, 2006

Related U.S. Application Data

(60) Provisional application No. 60/515,425, filed on Oct. 30, 2003.

(30) Foreign Application Priority Data

Mar. 28, 2003 (FI) ................................. 20030467

(51) Int. Cl.
*A61K 38/21* (2006.01)
*A61K 31/70* (2006.01)
(52) U.S. Cl. ........................................ 424/85.1; 514/47
(58) Field of Classification Search ........................ None
See application file for complete search history.

(56) References Cited

U.S. PATENT DOCUMENTS

2003/0053985 A1    3/2003  Shachar et al.

FOREIGN PATENT DOCUMENTS

| EP | 0 536 520 A1 | 4/1993 |
|---|---|---|
| WO | WO 98/33517 A1 | 8/1998 |
| WO | WO 01/23006 A1 | 4/2001 |
| WO | WO 02/080953 A2 | 10/2002 |

OTHER PUBLICATIONS

Savic et al, (1990), Immunology, 70:321-326.*

A. O. Shakil, "A Pilot Study of Interferon Alfa and Ribavirin Combination in Liver Transplant Recipients With Recurrent Hepatitis C", Hepatology, vol. 36, 2002, pp. 1253-1258.
E. Nemoto, et al., "Expression of CD73/ecto-5'-nucleotidase on human gingival fibroblasts and contribution to the inhibition of interleukin-1 α-induced granulocyte-macrophase colony stimulating factor production", Journal of Periodontal Research, vol. 39, 2004, pp. 10-19.
G. Kocić, et al., "Different responses of rat liver adenosine metabolizing enzymes during in vivo and in vitro treatment with interferon-α2b", Journal of Viral Hepatitis, vol. 5, 1998, pp. 353-356.
H. Liu, et al., "Interferon-β administration confers a beneficial outcome in a rabbit model of thromboembolic cerebral ischemia", Neuroscience Letters, vol. 327, 2002, pp. 146-148.
J. Niemelä, et al., "IFN-α Induced Adenosine Production on the Endothelium: A Mechanism Mediated by CD73 (Ecto-5'Nucleotidase) Up-Regulation", The Journal of Immunology, vol. 172, 2004, pp. 1646-1653.
K. Kalsi, et al., "Regulation of ecto-5'-nucleotidase by TNF-α in human endothelial cells," Molecular and Cellular Biochemistry, vol. 232, 2002, pp. 113-119.
L.D. Christensen, "Effects of Immunomodulators on Ecto-5'-Nucleotidase Activity on Blood Mononuclear Cells in Vitro," Scand. J. Immunol., vol. 35, 1992, pp. 407-413.
M. Kitakaze, et al., "Adenosine Therapy: A New Approach to Ischemic Heart Disease", abstract, p. A59.
J. A. Elias, et al., "Transgenic modeling of interleukin-13 in the lung," *Chest*, The Cardiopulmonary and Critical Care Journal, vol. 123, No. 3, Mar. 3, 2003, pp. 339S-345S.
V. Savic, et al., "Induction of ecto-5'-nucleotidase of rat cultured mesangial cells by interleukin-1β and tumour necrosis factor-α", Immunology 1990, vol. 70, pp. 321-326.

* cited by examiner

*Primary Examiner*—Prema Mertz
(74) *Attorney, Agent, or Firm*—Rothwell, Figg, Ernst & Manbeck p.c.

(57) ABSTRACT

This invention concerns a method of inducing an elevated level of adenosine in an individual by administering to said individual an effective amount of either i) recombinant protein CD73 or ii) a cytokine or another factor-being capable of inducing endothelial CD73 expression, or a combination thereof. Furthermore, the invention concerns a method for prevention or treatment of a disease or disorder requiring or benefiting from the elevation of the adenosine level in an individual, such as inflammatory conditions. Furthermore, the invention concerns a method of up-regulating endothelial CD73 expression in an individual by administering to said individual an effective amount of a cytokine or another factor being capable of inducing endothelial CD73 expression, and to a method for prevention or treatment of a disease or disorder requiring or benefiting from up-regulating endothelial CD73 expression.

10 Claims, 11 Drawing Sheets

METHOD FOR INDUCING AN ELEVATED LEVEL OF ADENOSINE IN AN INDIVIDUAL

CROSS-REFERENCE TO RELATED APPLICATION

The present application is a national stage filing under 35 U.S.C. §371 of PCT/FI2004/000158, filed on 19 Mar. 2004 which is a non-provisional of 60/515,425, filed 30 Oct. 2003, from which priority is claimed under 35U.S.C. § 119(e). The present application also claims priority to Finland patent application Ser. No. 20030467 filed on 28 Mar. 2003.

FIELD OF THE INVENTION

This invention relates to methods for inducing elevated adenosine levels in an individual and to treatment or prevention of diseases or disorders benefiting from an elevated adenosine level. The invention also concerns a method of up-regulating endothelial CD73 expression in an individual and to treatment or prevention of diseases or disorders benefiting from such CD73 up-regulation.

BACKGROUND OF THE INVENTION

The publications and other materials used herein to illuminate the background of the invention, and in particular, cases to provide additional details respecting the practice, are incorporated by reference.

The interaction between lymphocytes and endothelial cells is a multi-step process. To be able to penetrate the vessel wall and to reach the target site, circulating cells use a very finely regulated set of adhesion molecules. Enhanced adhesion to endothelium and subsequent transmigration of re-circulating leukocytes through the endothelial lining of vessel wall into the tissue is characteristic for inflammation. Moreover, the release of pro- and anti-inflammatory cytokines in a high extent takes place at sites of inflammation. Those cytokines are potent regulators of the expression of adhesion molecules.

CD73 (ecto-5'-nucleotidase) is a 70-kD glycosyl-phosphatidyl-inositol-anchored cell surface molecule with ecto-enzymatic activity. It is abundantly expressed on the vascular endothelium and at a low level on certain subpopulations of human lymphocytes. It is part of the purine salvage pathway by degrading nucleoside-5'-monophosphates (AMP and IMP) into nucleotides like adenosine and inosine (1).

Adenosine, a purine nucleoside product of the CD73 enzyme activity, binds to specific receptors on the cell surface. Adenosine is reported to have a role in many physiological and pathological events. So far four different subtypes of G protein-coupled adenosine receptors A1R, A2aR, A2bR and A3R have been cloned. Due to the diversity of the receptors and their abundant localization in different tissues, adenosine-adenosine receptor interaction leads to various physiological responses. Adenosine, by binding to A1 and A2 receptors, regulates pathological consequences of inflammation by controlling leukocyte binding to endothelium and acts as an anti-inflammatory agent by binding to A2 and A3 receptors, through the inhibition of neutrophil degranulation (2). Adenosine also decreases eosinophil migration through activation of A3 receptor. This promoting effect of 5'-AMP is CD73 mediated and is followed by an increase in intracellular cAMP. Recently, a critical role for A2a receptor has been shown in decreasing systemic and tissue specific inflammatory responses in vivo.

Adenosine prevents cell damage during heart and central nervous ischemia (3-5). After hypoxia ecto-5'-nucleotidase activity increases due to phenomenon known as preconditioning. This results in release of large amounts of adenosine leading to increased resistance of cells to infarction for example in cardiac hypoxia.

So far, practically nothing is known about the regulation of endothelial CD73 expression and function. However, in inflammation there may be some inducers secreted which in vivo specifically control endothelial CD73 expression.

As adenosine, having an anti-inflammatory and cell protective effect, plays an important role in controlling the extent and consequences of inflammation, this work was designed to identify factors responsible for the regulation of CD73 expression as well as ecto-5'-nucleotidase mediated adenosine production.

Adenosine as such could be administered to patients suffering from inflammatory conditions or conditions that untreated most likely would lead to tissue inflammation. However, a serious drawback by direct administration of adenosine is the rapid elimination of adenosine in vivo. Therefore, this work offers a new way to achieve elevated levels of adenosine over a prolonged time.

OBJECTS AND SUMMARY OF THE INVENTION

The main object of the present invention is to provide a method for increase of the adenosine level in an individual and for maintaining the elevated adenosine level over a prolonged period of time and thereby prevent or treat inflammatory conditions or conditions that untreated would lead to tissue inflammation.

Another object of this invention is to provide a method for up-regulating the expression of endothelial CD73 in an individual and for preventing or treating diseases or disorders benefiting from such CD73 up-regulation, that necessary not would require an elevated level of adenosine.

Thus, according to one aspect, this invention concerns a method of inducing an elevated level of adenosine in an individual by administering to said individual an effective amount of either i) recombinant protein CD73 or ii) a cytokine or another factor being capable of inducing endothelial CD73 expression, or a combination thereof.

According to another aspect, the invention concerns a method for prevention or treatment of a disease or disorder requiring or benefiting from the elevation of the adenosine level in an individual, by administering to said individual an effective amount of either i) recombinant protein CD73 or ii) a cytokine or another factor being capable of inducing endothelial CD73 expression, or a combination thereof.

According to a third aspect, the invention concerns a method of up-regulating endothelial CD73 expression in an individual by administering to said individual an effective amount of a cytokine or another factor being capable of inducing endothelial CD73 expression.

According to a fourth aspect, the invention concerns a method for prevention or treatment of a disease or disorder requiring or benefiting from up-regulating endothelial CD73 expression in an individual, by administering to said individual an effective amount of a cytokine or another factor being capable of inducing endothelial CD73 expression.

BRIEF DESCRIPTION OF THE DRAWINGS

FIG. 3 is a graphic presentation of the relative expression CD73 mRNA in HUVEC. HUVEC were incubated with or without IFN-alpha for 72 hours. Real-time RT-PCR analyses were performed with TaqMan. The figure represents the relative expression of CD73 mRNA between control and IFN-alpha treated cells. Normalization was performed using housekeeping gene GAPDH. The data present the means of three experiments made in duplicates±SEM, * P<0.05.

FIG. 6 shows microscopy photographs demonstrating the effect of IFN-α on expression of CD73 in bladder carcinoma. (a) A bladder cancer specimen stained with anti-CD73 mAb 4G4 before IFN-α treatment. Some vessels are faintly or moderately expressing CD73. (b) The same tumour stained with anti-CD73 mAb 4G4 after IFN-alpha treatment. Vessels express CD73 moderately or abundantly. (c) Staining with a negative control antibody 3G6. d-f, An example of a tumour (t) expressing CD73 before (d) and after (e) IFN-alpha treatment. Also in this case IFN-alpha increased CD73 expression on endothelial cells. (f) Negative control staining. Some vessels are marked with arrows. Original magnification 100×, scale bar 20 μm.

FIG. 7 shows that IFN-α increases cell-surface ecto-5'-nucleotidase activity. HUVEC (a) and PBL (b) were pre-treated for 48 hours without (open bars) or with 1000 U/ml IFN-α (closed bars). Ecto-5'-nucleotidase activity was assayed by using 300 μmol/L [$^3$H]AMP and expressed on ordinate as nmoles of substrate dephosphorylated by $10^6$ cells per hour (mean±SEM; n=4-5). *P<0.05 as compared to control cells. (c) Rate of [$^3$H]AMP hydrolysis by control (closed circles) and IFN-α-treated HUVEC (open circles) versus substrate concentration plot. Values are expressed as mean±SEM for two independent experiments. The kinetic parameters ($V_{max}$ and $K_m$) were calculated from the presented curves and summarized in the text.

FIG. 8 shows the effect of IFN-α on permeability of HUVEC monolayers. a, HUVEC were plated on porous polystyrene membrane (pore size of 0.4 μm) and grown to confluency. HUVEC were grown in medium or treated with 100 U/ml IFN-α for 72 hours. Fifteen minutes after adding AMP, the membrane function was analyzed by measuring the flux of 70 kDa FITC-dextran through HUVEC monolayer to the lower chamber with a fluorometer. The FITC-dextran flux was measured up to 100 min. Values are means±SEM, n=3. *P<0.05 as compared to IFN-α treated cells. b, Confluent monolayers were exposed to AMPCP (100 μM), a specific ecto-5'-nucleotidase inhibitor, 30 min before addition of FITC-dextran. Data shown are mean values±SEM, n=3. *P<0.05 as compared to IFN-α treated cells.

FIG. 10 shows metabolic pathways regulating adenosine levels. The enzymatic reactions leading to the formation and degradation of adenosine are depicted. The amount of adenosine can be elevated by 1. upregulating/increasing amount of CD73; 2. providing more AMP; 3. inhibiting adenylate kinase, and 4. inhibiting adenosine deaminase, or combinations thereof.

DETAILED DESCRIPTION OF THE INVENTION

This invention is based on screening of a range of potential mediators and finding that IFN-α, β and gamma are potent activators of CD73 expression. IFN-alpha was chosen for more detailed studies. IFN-α produced specific time and dose-dependent in vitro upregulation of CD73 expression on endothelium but not on PBL and even more importantly, it upregulated CD73 expression in tumour vessels of bladder carcinoma patients in vivo. Upregulation of endothelial CD73 after IFN-α induction was enzymatically functional producing adenosine from 5'-AMP leading to enhanced barrier function in endothelial cells. Moreover, a cell type specific difference in regulation of endothelial and lymphocyte CD73 was found.

The results of the distinct effects of IFN-α on endothelial and lymphocyte CD73 further demonstrate the difference between the cell types to regulate the expression of CD73. In this context it is worth mentioning that the amount of CD73 varies markedly between lymphocytes and endothelial cells. Only 10 to 15% of lymphocytes express CD73 and the expression level is low in comparison to e.g., HUVEC which all are positive for CD73. This type of cell specific differences in amount and regulation of CD73 may be fundamental for appropriate behaviour of lymphocytes, the role of which is to actively deaminate the existing adenosine and extravasate to lymphoid tissues or to sites of inflammation. In contrast, adenosine is necessary for endothelial cells to maintain their barrier function.

In conclusion, this work demonstrates how CD73 can be upregulated both in vitro and in vivo by cytokines, especially interferons. As adenosine is highly anti-inflammatory in its nature, manipulation of its endogenous production via upregulation of CD73 may be a potential way to treat harmful inflammatory conditions such as e.g., reperfusion injuries in connection to myocardial infarction and stroke, organ transplantations and various tissue damages and traumas.

DEFINITIONS

As used herein, the term "mediator" is meant to include any soluble factor that has an effect in the setting of inflammation. As used herein, the term "induce" is further meant to mean a factor that increases expression and enhances function of certain molecules.

The tem "treatment" or "treating" shall be understood to include complete curing of a disease or disorder, as well as amelioration or alleviation of said disease or disorder.

The term "prevention" shall be understood to include complete prevention, prophylaxis, as well as lowering the individual's risk of falling ill with said disease or disorder. This term shall also be understood to include preconditioning of tissue by elevating the adenosine level according to the method of this invention at a very early stage (e.g. before operations, before complete diagnosis at stroke and infarct patients) so as to prevent the tissue from damages.

The term "individual" refers to a human or animal subject.

The expression "effective amount" is meant to include any amount of an agent according to the present invention that is sufficient to bring about a desired therapeutical result, especially upon administration to an animal or human subject.

The wording "elevated level of adenosine" shall be interpreted as an adenosine level that is at least 2% higher, preferably at least 20% higher, most preferably at least 30% higher than the normal tissue level would be without the measures taken according to this invention.

The wording "disease or disorder requiring or benefiting from an elevation of the adenosine level" means that the prevention or treatment of said disease or disorder is facilitated by an elevated adenosine level.

The wording "disease or disorder requiring or benefiting from up-regulating endothelial CD73 expression" means that the prevention or treatment of said disease or disorder is facilitated by such up-regulation.

The expression "inflammatory condition" is meant to include any harmful and undesired inflammatory response in a tissue in an individual, wherein said inflammatory condition may result from an acute condition such as tissue trauma, a reperfusion injury resulting from myocardial infarction or stroke, organ transplantations or an other surgical operation, or from a chronic condition including allergic conditions, autoimmune diseases, and inflammatory diseases.

Treatment of tissue traumas or reperfusion injuries shall in this invention particularly be understood as prevention of inflammatory conditions that most likely will follow if said traumas or reperfusion injuries are left untreated.

Preferable Embodiments:

Although an elevated level of adenosine in an individual can be induced by administering the recombinant CD73 protein, or by a cytokine or another factor capable of inducing endothelial CD73 expression or by a combination of both therapies, the use of a cytokine or another factor with similar capability in many cases would be preferable. However, in serious traumas administration of recombinant CD73 protein would be useful, in order to rapidly achieve an increased adenosine production, as an alternative or as an additional therapy.

Suitable agents to be used in this invention include cytokines or other factors that directly or indirectly upregulate transcription of the CD73 gene. A suitable cytokine for use in this invention is typically an interferon or an interleukin, but also other agents may be used. In case the cytokine is an interferon, the interferon may be alpha-, beta-, gamma-, omega-, or any other interferon and it can be any subtype of the aforementioned interferons. It is believed that particularly alpha- and beta-interferons are suitable for use in this invention.

Any interleukin capable of inducing endothelial CD73 expression is also suitable for use in this invention. As examples of such interleukins can be mentioned IL-4, IL-10, IL-13 and IL-20.

Typical diseases or disorders requiring or benefiting from elevation of the individual's adenosine levels are: tissue trauma; reperfusion injuries resulting from myocardial infarction or stroke, organ transplantations or other surgical operations; cancer or cancer metastasis; or inflammatory conditions resulting from the aforesaid traumas or reperfusion injuries or from chronic conditions including allergic conditions, autoimmune diseases, and inflammatory diseases. As examples of such chronic conditions can be mentioned arthritis, allergic conditions such as asthma, inflammatory conditions such as inflammatory bowel disease or an inflammatory condition of the skin, psoriasis, Parkinson's disease, Alzheimer's disease, autoimmune diseases, type I or type II diabetes, atherosclerosis, multiple sclerosis, Crohn's disease, or rejection reactions due to organ transplantations.

According to a particularly preferable embodiment, the administration of recombinant CD73 protein or a cytokine or both is combined with an administration of adenosine monophosphate (AMP) in order to safeguard the source for adenosine to be produced as result of the elevated CD73 level, obtained by elevated expression or by direct administering of the recombinant CD73 protein.

According to another preferable embodiment, the administration of recombinant CD73 protein or a cytokine or both is combined with an administration of an adenylate kinase inhibitor, which prevents AMP from conversion into adenosine diphosphate (ADP) or adenosine triphosphate (ATP). A combined administration of recombinant CD73 protein or a cytokine or both, with AMP and such an adenylate kinase inhibitor may be particularly preferred.

According to still another preferred embodiments, the administration of recombinant CD73 protein or a cytokine or both is combined with an administration of an adenosine deaminase inhibitor which prevents the decomposition of adenosine. This could also further be combined with administration of AMP and optionally also an adenylate kinase inhibitor which prevents AMP from conversion into adenosine diphosphate (ADP) or adenosine triphosphate (ATP).

Figure 10:
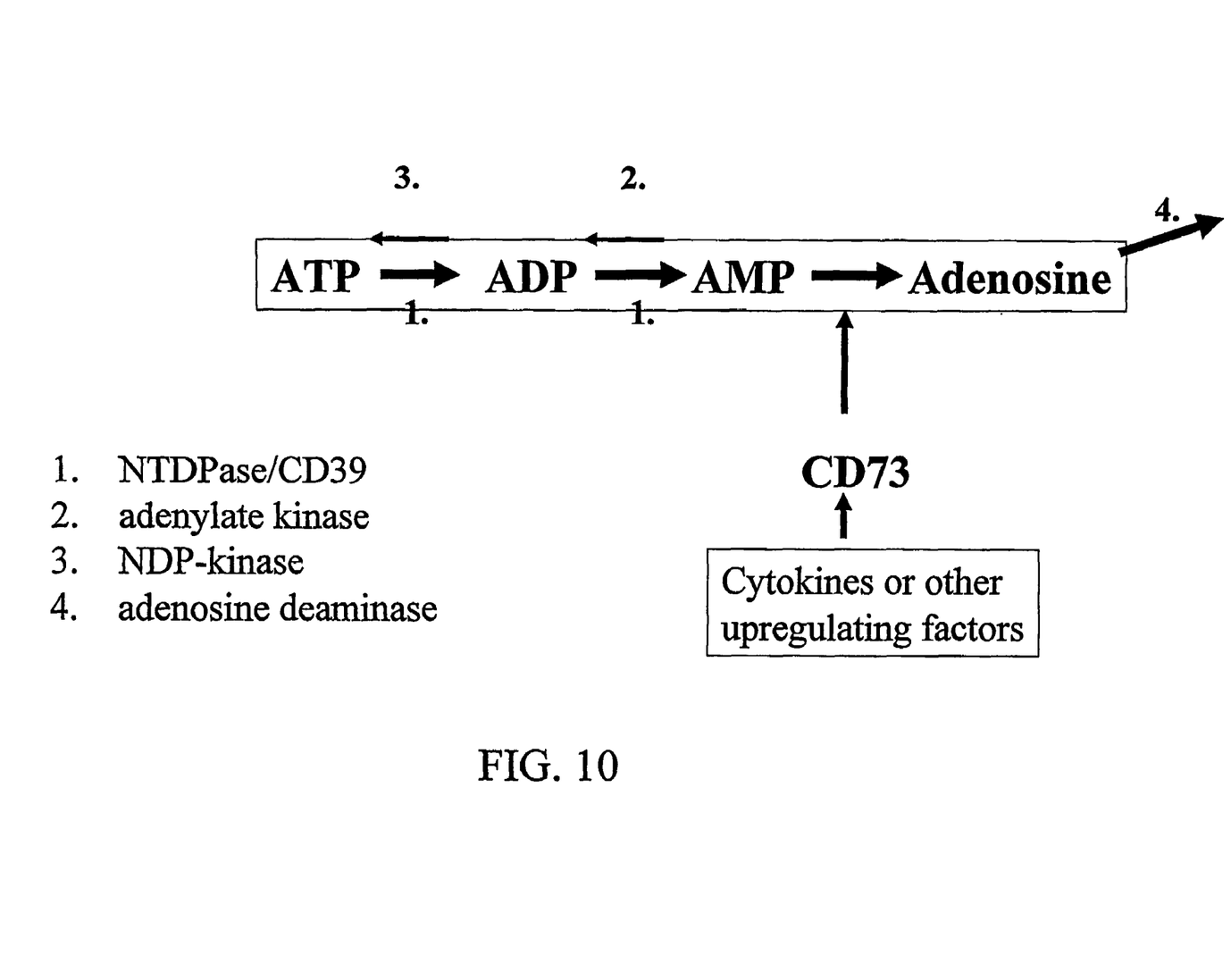

The metabolic pathways regulating adenosine levels are shown in FIG. 10.

According to another preferable embodiment, administering of recombinant CD73 protein or a cytokine or both, optionally in combination with administration of adenosine monophosphate, is started as soon as a trauma patient or infarction or stroke patient is brought to care, optionally even if the final diagnosis is not fully clarified. Hereby the adenosine level can be increased as rapidly as possible. In case of surgical operations it may be useful to start administering of recombinant CD73 protein or a cytokine or both, optionally in combination with administration of adenosine monophosphate, already before the operation, for example 12 h before the start of the operation. Also in these cases an adenylate kinase inhibitor and/or an adenosine deaminase inhibitor could be administrated in addition to the agents mentioned above.

Therapeutically Effective Amounts, Administration Routes and Dosage Forms:

The therapeutically effective amount of the components according to this invention to be given to a patient in need of such treatment may depend upon a number of factors including, for example, the age and weight of the patient, the precise condition requiring treatment and its severity, and the route of administration. The precise amount will ultimately be at the discretion of the attending physician. Thus, practice of the present invention may involve any dose, combination with other therapeutically effective drugs, pharmaceutical formulation or delivery system for oral, topical, inhalation or parenteral administration.

Amounts and regimens for the administration of the agents according to the present invention can be determined readily by those with ordinary skill in the art of treating inflammation-related disorders, such as reperfusion injuries, stroke, organ transplantation, traumas, cancer or cancer metastasis, or chronic inflammatory diseases.

Based on this invention it can be assumed that e.g. subcutaneously, intramuscularly, intravenously or transdermally given cytokines, such as interferons, or other factors induce upregulation of CD73 and thus increase local concentration of adenosine, which is anti-inflammatory. This overcomes the problems related to the use of adenosine, which has a very short half-life and is therefore, not optimal for therapeutic use.

The cytokines or other factors may according to the present invention preferably be administered by infusion or by injection. Intravascular infusions are normally carried out using parenteral solutions contained within an infusion bag or bottle, and may be connected to different systems to control the rate of administration of the parenteral solution. The cytokines or other factors may according to the present invention alternatively be administered as an aerosol.

Preferred formulations for infusion or injection may include carriers, such as human serum albumin, pharmaceutically acceptable salts, buffers, such as phosphates and/or other pharmaceutically acceptable excipients. The active ingredient, e.g. the cytokines or other factors may be provided in amounts ranging from e.g., $1-50 \times 10^6$ IU per ml. The formulation may preferably be provided as lyophilised powder in dosage form, to be prepared by the addition of water or other solutions suitable for injection prior to the administration.

Cytokines, such as interferons, or other factors with similar capability can be given to the patients suffering from or being at risk of getting inflammations. Those types of inflammatory conditions are for example ischemia reperfusion injuries during the stroke and myocardial infarction. Also organ transplantation and trauma are occasions often associated with major inflammatory components. Due to their unique characteristics different cytokines have their preferential disease targets: beta interferons are the most suitable interferons for ischemia reperfusion injuries in stroke and myocardial infarction, whereas alfa-interferons may not be the drug of choice in myocardial infarction.

In case the recombinant CD73 protein is administered, a suitable administration route would be infusion or injection. A suitable daily dose is in the range 0.1 to 5.0 mg/kg body weight.

The adenosine monophosphate may be administered e.g. subcutaneously, intramuscularly, intravenously or transdermally. A typical daily dose may be in the range 0.1 to 100 mg/kg body weight.

Also an optionally used adenylate kinase inhibitor or an adenosine deaminase inhibitor may be, for example, administered subcutaneously, intramuscularly, intravenously or transdermally. A typical daily dose of such inhibitors may be in the range 0.1 to 100 mg/kg body weight.

The invention will be illuminated by the following non-restrictive Experimental Section.

EXPERIMENTAL SECTION

In the following examples, given to further describe the invention in detail, the following materials and methods were used.

Cells, antibodies and reagents. Human umbilical vein endothelial cells (HUVEC) were isolated and cultured on gelatin-coated cell culture flasks in complete medium. Human peripheral blood lymphocytes (PBL) from healthy volunteers were isolated using Ficoll-Hypaque (Histopague-1077; Pharmacia, Uppsala, Sweden). PBL, U266B1 cell line, and the HEC endothelial cell line (equivalent to EaHy-926) were cultured in RPMI 1640 medium containing 10% FCS, 4 mM L-glutamine, 100 U/ml penicillin, and 100 µg/ml streptomycin. Anti-CD73 mAb 4G4 (mouse IgG1), anti-ICAM-1 mAb 5C3 (IgG1) and mAb 3G6 (mouse IgG1) against chicken T-cells as a negative control antibody were used. α,β methyleneadenosine 5'-diphosphate (AMPCP) and adenosine 5'-monophosphate (5'-AMP) were from Sigma (Sigma Chemical Co., St. Louis, Mo.).

Inductions and immunofluorescence stainings. Details about inductions are indicated in Table 1. For every timepoint, a control flask was incubated without inducers.

Three different protocols were used for immunofluorescence stainings:

A) To study the effect of a panel of different inducers on surface expression of CD73 immunofluorescence analyses were performed. In brief, HUVEC were treated with or without inducers and detached with 5 mM EDTA-trypsin. $5 \times 10^5$ cells for each staining were incubated with saturating concentrations of mAb 3G6 (neg co), 4G4 (anti-CD73) and 5C3 (anti-ICAM-1) as hybridoma supernatants or purified antibody (final concentration, 10 micrograms/ml) for 20 min at 4° C. and washed twice. Then the cells were incubated for 20 min at 4° C. with 1:100 diluted FITC-conjugated sheep anti-mouse-IgG mAb (Sigma) containing 5% AB-serum. Finally the cells were washed twice and fixed with 1% paraformaldehyde. All incubations and washes were performed with phosphate-buffered saline (PBS) containing 2% FCS and 1 mM NaN3. Fluorescence was then detected using fluorescence activated cell sorter (FACS, Becton-Dickinson, San Jose, Calif.). The difference between control and treated cells was calculated from:

$$\text{Fold difference} = \frac{\text{Treated cells}(MFI, \alpha CD73 - MFI, neg.co)}{\text{Non treated cells }(MFI, \alpha CD73 - MFI, neg.co)}$$

B) For the detection of intracellular CD73, lymphocytes were permeabilized before immunofluorescence stainings by incubating them for 2 min in acetone at −20° C. Then the cells were washed with RPMI 1640 medium containing 5% FCS and stained and analysed by FACS as described in (A).

C) To study the distribution of CD73 on HUVEC or PBL, cells were first stained as in A) and then spun using 1000 RPM for 5 minutes onto a glass-slide, fixed with formaldehyde and mounted with Fluoromount-G (Southern Biotechnology Associates, Inc., Birmingham, Ala.). Alternatively, HUVEC monolayers were grown on gelatin coated glass slides and stained for CD73, ICAM-1 or negative control by incubating cells with saturating concentrations of mAbs as described in (A) and analyzed with a fluorescence microscope (Olympus BX60).

CD73 RNA analysis. HUVEC were grown to confluency in cell culture flasks and PBL were isolated prior to inductions using Ficoll-Hypague. $1\times10^7$ cells of both HUVEC and PBL were incubated with IFNalpha 1000 U/ml in culture medium. A similar number of cells was left untreated. RNA was isolated using UltraspecTM-II RNA Isolation System (Biotecx Laboratories, Inc., Houston, Tex.) according to the instructions of the manufacturer. 1-2 μg of total RNA was Dnase I treated (Amplification Grade, Gibco BRL, Life Technologies, Gathersburg, Md.). cDNA was made by using Superscript II Reverse Transcriptase (Gibco BRL, Life Technologies) according to the manufacturer's instructions. Prior to real-time RT-PCR measurement, samples were treated with Rnase H (Gibco BRL, Life Technologies). Primers and probes for GAPDH housekeeping gene were used as internal controls. CD73 primers and probes were designed using Primer Express computer software (PE Biosystems, Foster City, Calif.). CD73 primers 5'CTG GGA GCT TAC GAT TTT GCA3' and 5'CCT CGC TGG TCT GCT CCA3' and CD73 probe 5'CCA ACG ACG TGC ACA GCC GG3' were used (MedProbe, St. Hanshaugen, Norway). The real-time RT-PCR measurements were performed using TaqMan® Universal PCR Master Mix (Applied Biosystems, Branchburg, N.J.) and ABI PRISM 7700 Sequence Detector (Applied Biosystems). The expression of the housekeeping gene GAPDH was used as a reference for normalization and the relative increase of CD73 mRNA expression between control and IFN-α treated cells was calculated.

Ecto-5'-nucleotidase assay. Ecto-5'-nucleotidase activity was assayed by thin layer chromatography (TLC) as described previously (19). Briefly, the standard enzyme assay contained in a final volume of 120 μl RPMI 1640, $4-6\times10^4$ detached HUVEC (or $1\times10^5$ lymphoid cells), 5 mmol/L β-glycerophosphate, and the indicated concentrations of 5'-AMP with tracer $[^{2-3}H]$AMP (specific activity 18.6 Ci/mmol; Amersham). Incubation times were chosen to ensure the linearity of the reaction with time, so that the amount of the converted AMP did not exceed 7-10% of the initially introduced substrate. Aliquots of the mixture were applied to Alugram SIL G/UV254 TLC sheets (Macherey-Nagel) and separated with isobutanol/isoamyl alcohol/2-ethoxyethanol/ammonia/H20 (9:6:18:9:15) as solvent. $^3$H-labeled AMP and its dephosphorylated nucleoside derivatives were visualized in UV light and quantified using a Wallac-1409 β-spectrometer.

Permeability assays. To evaluate barrier function of confluent monolayers, HUVEC were seeded (50 000 cells/insert) on Transwell insert polycarbonate filters (6.5-mm diameter, 0.4-μm pore size; Costar, Cambridge, Mass.). The filters were treated for 1-2 h with fibronectin and air-dried before seeding endothelial cells. Typically, monolayers were studied 4-5 days post seeding. HUVEC were either induced with IFN-α (100 U/ml) for 72 hours before the studies of monolayer permeability or grown in medium without IFN-α. Transport across endothelial monolayers was assessed by measuring the flux of FITC-labeled dextran (500 μg/ml, mol wt 70 000). Endothelial monolayers were pre-treated with AMP (50 μM) for 15 min before the FITC-dextran transport was initiated. To evaluate the role of CD73 enzymatic activity on the endothelial cell permeability, the flux of FITC-dextran was measured in the presence or absence of a specific inhibitor of ecto-5'-nucleotidase, AMPCP (100 μM). In certain experiments, AMPCP was added to the upper and lower chambers 30 min before the transport was initiated by adding FITC-labeled dextran. The inserts were removed from the bottom chamber (Visiplate, Perkin Elmer Life Sciences) at the time points 10 min, 20 min, 30 min, 40 min and 100 min and FITC-labelled dextran was measured directly from the bottom chambers in a fluorometer (TECAN Ultra fluorescence reader, Tecan, Austria) using 485 and 535 nm as the excitation and emission wavelengths, respectively.

Statistical analysis. Data are presented as mean±SEM of individual experiments. Statistical comparisons were made using Student's T-test, and P values<0.05 were taken as significant. Data from kinetic experiments were subjected to computer analyses using the Michaelis-Menten equation to determine the $K_m$ and $V_{max}$ values (GraphPad Prism™ version 3.0, San Diego Calif.).

EXAMPLE 1

Upregulation of CD73 Expression on Endothelial Cells

Figure 1:
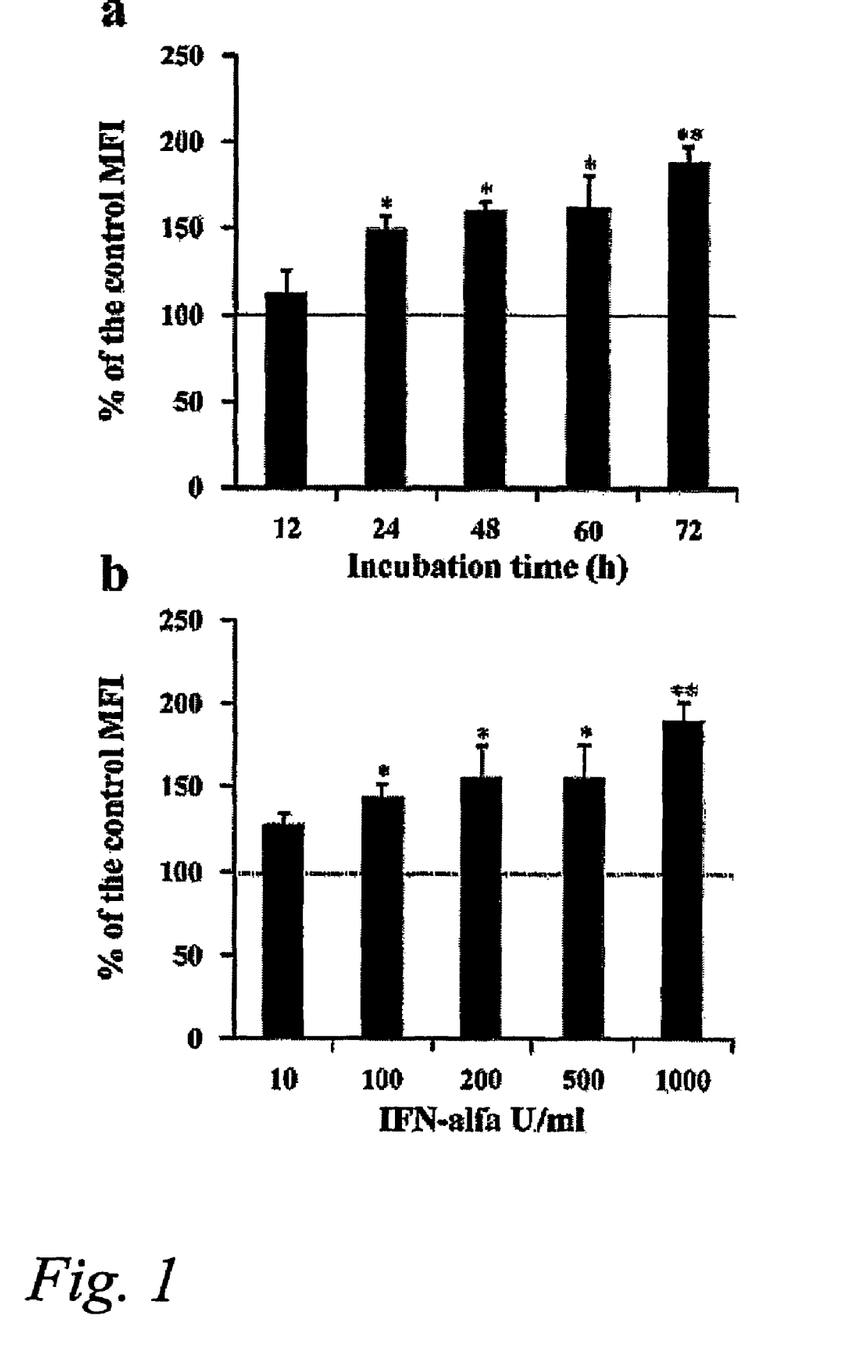
FIG. 1 is a graphic presentation showing that the induction of CD73 surface expression on HUVEC by IFN-α is both time and dose-dependent. In Panel (a) HUVEC were exposed to 1000 U/ml IFN-α for indicated time periods. (b) HUVEC were cultured with different concentrations of IFN-α for 72 hours. Relative means of MFI±SEM of 3-9 experiments are shown. Control expression is the expression of CD73 without IFN-α at each time point. Background (the negative control staining) is subtracted. *P<0.05; ** P<0.01
Figure 9:
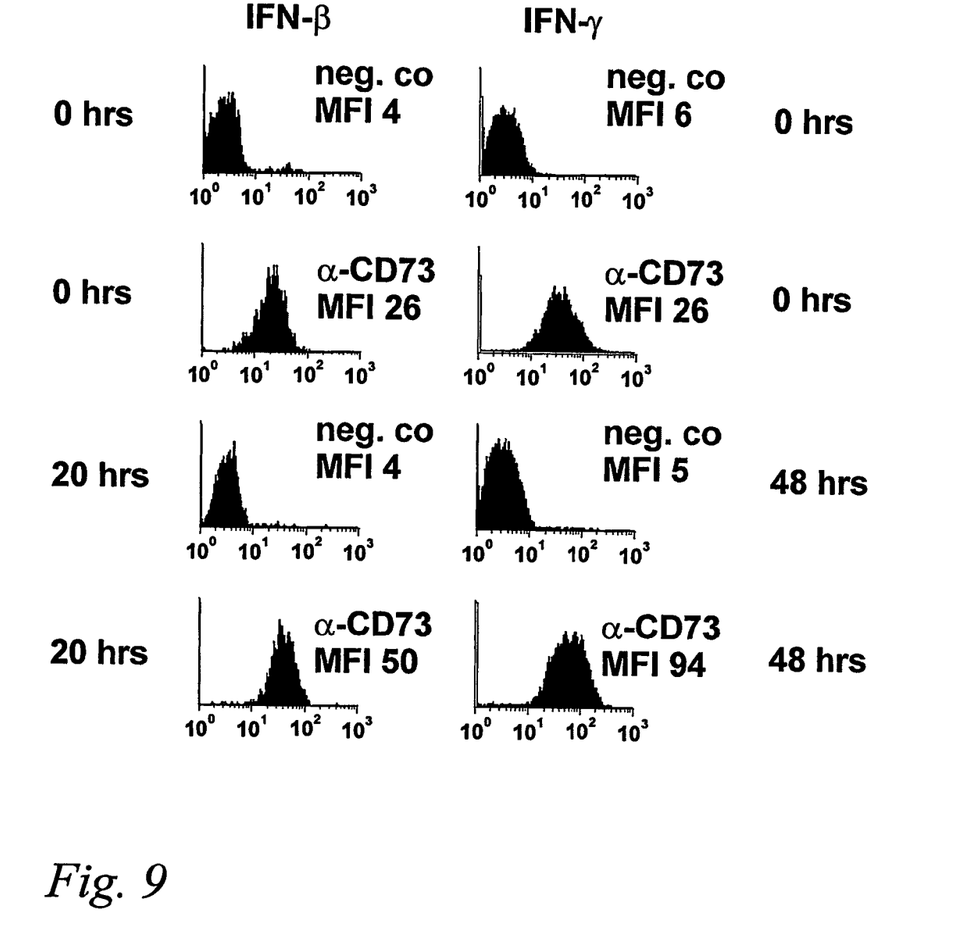
FIG. 9 are representative histograms depicting CD73 upregulation on human umbilical endothelial cells after incubation with IFN-β and -γ. During 20 hours of incubation IFN-β increased the mean fluorescence intensity (MFI) from 26 to 50, while during 48 hours of incubation IFN-γ upregulated the MFI from 26 to 94. X-axis is the fluorescence intensity in a logarithmic scale and y-axis is the relative number of cells.

This work was designed to find potent regulators of CD73 expression or CD73 based ecto-5'-nucleotidase enzyme activity. Thus endothelial cells were exposed to a wide range of well-known inducers of various molecules (Table 1). The inducers included for example interferons and LPS. The presence of interferons (IFN-α, IFN-β and IFN-γ) led to a marked upregulation in the CD73 expression on HUVEC with doses of >200 U/ml after induction for 20-24 hours (FIGS. 1 and 9).

This example shows that CD73 expression is upregulated on endothelial cells with interferons. As IFN-α is rather widely used in the clinical medicine, its effects were evaluated in more detail.

TABLE 1

Regulators used to induce CD73 expression

| Inducer | Concentration used | Incubation time |
| --- | --- | --- |
| Rapidly acting | | |
| FMLP | $10^{-9}$ and $10^{-7}$ M | 5 min and 2 h |
| db cAMP | 0.5 and 5 microg/ml | 5 min and 2 h |
| histamine | 1 and 10 microg/ml | 5 min and 2 h |
| PMA | 1 and 10 ng/ml | 5 min and 2 h |
| Slowly acting | | |
| LPS | 1 and 100 ng/ml | 4 and 20 h |
| | 100 and 500 ng/ml | 48 h |
| IFN-alpha | 1, 5, 10, 50, 100, 200, 500 and 2000 U/ml | 72 h |
| | 1000 u/ml | 4, 12, 20, 24, 48, 60, 72 and 96 h |
| IFN-gamma | 50 and 200 U/ml | 4 and 20 h |
| | 1000 U/ml | 12, 20, 24, 40, 48, 60 and 72 h |
| IFN-β | 1000 U/ml | 20, 24, 40, 48 and 72 h |

FMLP = formylated methionoine-leucine phenylalanine
PMA = phorbol myristate actetate
LPS = lipopolysaccharide

EXAMPLE 2

Time and Dose Dependence of the Upregulation by IFN-α

Practically all non-activated HUVEC bear CD73 on their surface when analysed by FACS. Therefore to measure the increase in expression of CD73 molecules on cell surface the mean fluorescence intensity (MFI) of HUVEC was analysed.

To further study the kinetics of IFN-α upregulation, confluent monolayers of HUVEC were incubated using different doses of IFN-α for the indicated periods of time. CD73 expression was increased time-dependently almost two fold (92.4±11.5%; n=9) after 72 hours with 1000 U/ml IFN-α (FIG. 1a). Longer exposure of the HUVEC to IFN-α did not cause further significant increase in CD73 expression (data not shown). A similar pattern of CD73 upregulation was seen after induction with IFN-β and IFN-γ (FIG. 9). Upregulation of CD73 expression was also dose dependent, as in concentrations ranging from 10 to 1000 U/ml the highest increase in intensity was observed at 1000 U/ml (FIG. 1b).

Figure 2:
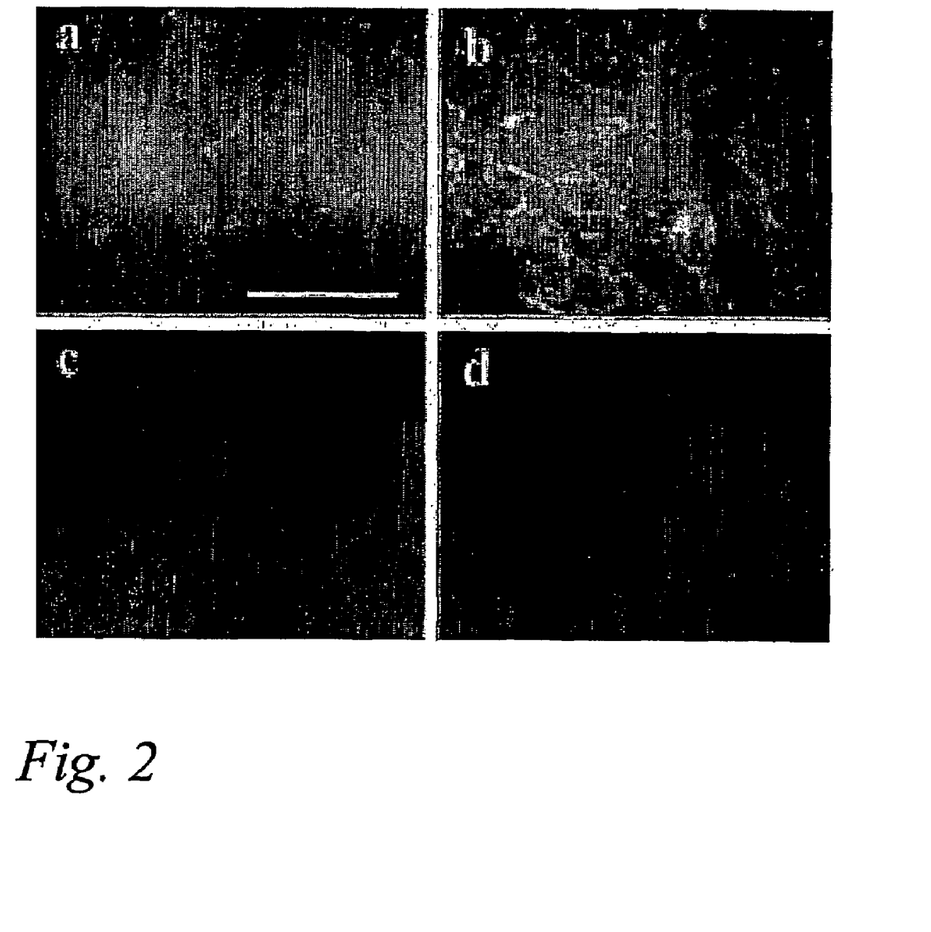
FIG. 2 is a microscopy photograph demonstrating that the induction of CD73 with IFN-alpha leads to increased expression rather than changes in its distribution. HUVEC were either grown in medium or induced with IFN-alpha for 72 hours and the cell surface expression of CD73 was detected with mAb 4G4 against CD73 and FITC conjugated anti-mouse IgG antibody. (a) On control HUVEC CD73 is expressed on the cell surface in a punctate like pattern. (b) After IFN-α induction CD73 is more intense, but surface distribution is similar as on control HUVEC. Staining with a negative control antibody 3G6 on control HUVEC (c) and after IFN-α induction (d). Original magnification 400×, Scale bar 10 μm.

Immunofluorescence stainings followed by fluorescence microscopy revealed that IFN-α treatment does not induce any significant changes in the distribution or polarization of CD73 on HUVEC surface. Instead, CD73 is more intensely but similarly distributed on the cell surface (FIG. 2).

This example shows that IFN-α increases endothelial CD73 expression in a time and dose dependent manner.

EXAMPLE 3

Effect of IFN-α on CD73 RNA Expression

Figure 3:
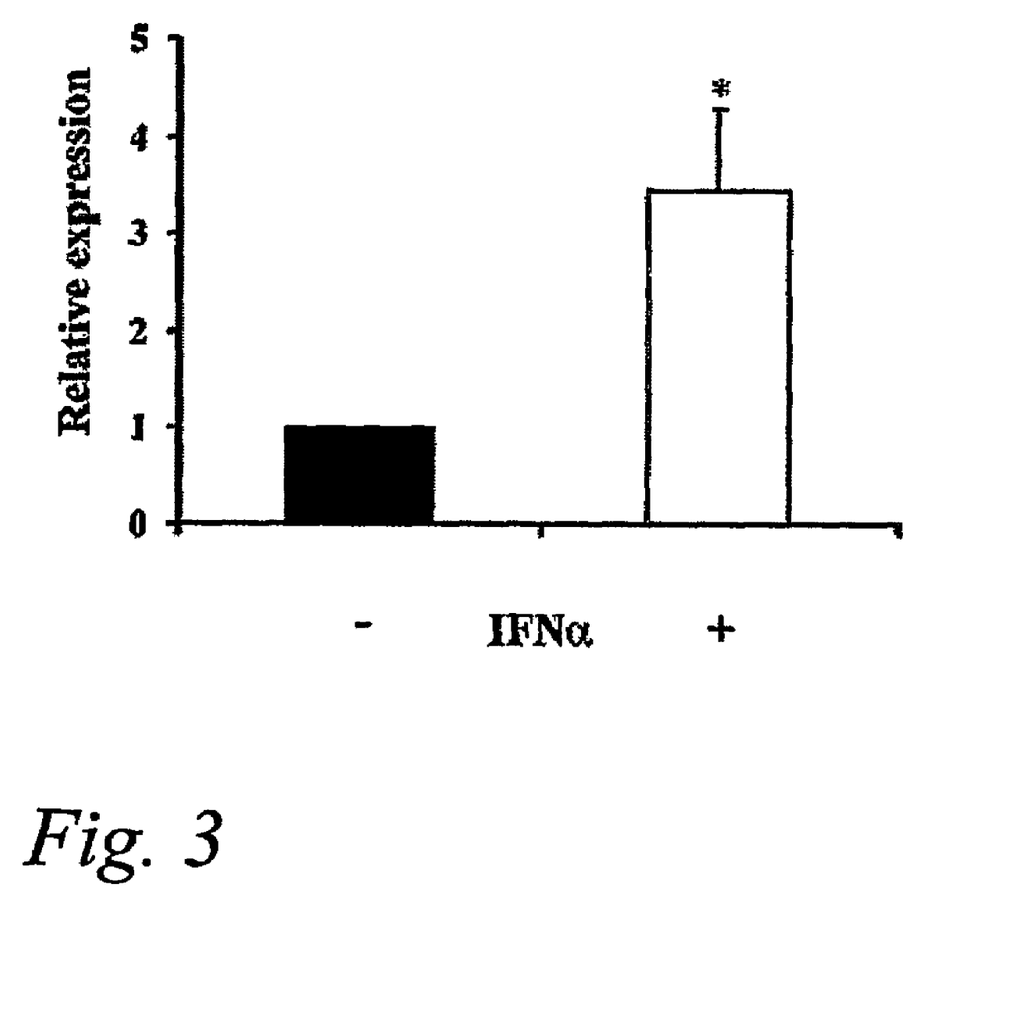

Next, it was determined whether increase in CD73 expression is mediated by increase in CD73 RNA expression. After 72 hours induction of HUVEC with 1000 U/ml IFN-α, CD73 RNA level was 3.4±0.5 (mean of relative expression±SEM; n=3) compared to control cells after normalization to GAPDH (FIG. 3).

This confirms that the increase in CD73 expression observed in Example 1 indeed is mediated by an increased RNA expression.

EXAMPLE 4

Cell-type Specificity of the Upregulation

Figure 4:
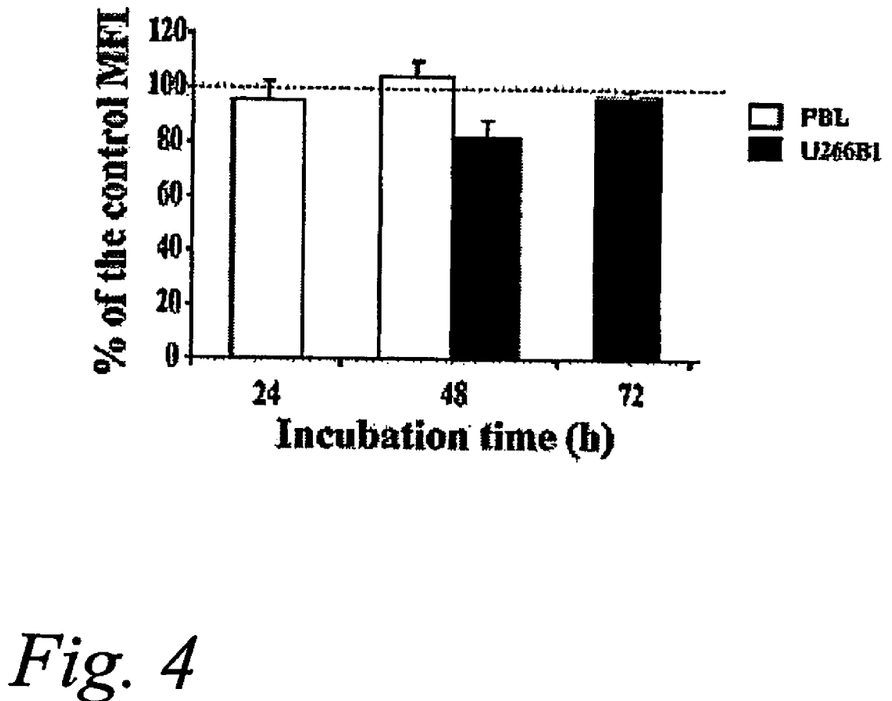
FIG. 4 is a graph showing that the regulation of lymphoid CD73 expression differs from that of endothelial cells. U266B1 cells and PBL were grown in medium with or without 1000 U/ml IFN-α for different times. No significant changes are seen on PBL (white bars) or U266B1 (black bars) when exposed to IFN-α for indicated periods of time when compared to non-treated control cells. Relative means of MFI±SEM of 3-6 experiments/timepoint are shown.

Despite the structural similarity of endothelial and lymphoid CD73, IFN-α promotes different effects on these two cell-types. After finding out that CD73 expression on endothelial cells is IFN-α inducible it was determined whether CD73 on lymphocytes would also behave similarly in the same conditions. 1000 U/ml IFN-α did not increase CD73 expression on PBL significantly (FIG. 4). Even with longer induction time up to 48 hours minor changes in CD73 expression on lymphocyte surface was observed. To exclude the possibility that freshly isolated lymphocytes do not survive well in culture conditions and therefore, fail to upregulate CD73, CD73 expressing lymphoid cell line U266B1 was also treated with IFN-α. They also were incapable of upregulating their CD73 expression even after 48 or 72 hours of induction. Instead, there was a decrease at 48 hours time-point after IFN-α treatment as compared to control cells (relative MFI 82.1±5.6% vs. 100%; n=3) (FIG. 4).

To elucidate whether there is also upregulation in intracellular CD73 protein level, PBL and HUVEC were permeabilized with acetone before immunofluorescence staining after IFN-α induction. No upregulation of intracellular expression of CD73 could be observed in PBL. Similar results were obtained when analyses were done with FACS and fluorescence microscopy. In HUVEC a slightly increased intracellular staining with anti-CD73 mAb was seen after IFN-α induction (data not shown).

EXAMPLE 5

CD73 Expression in Clinical Tumor Samples

To investigate whether IFN-α would also regulate the expression of CD73 in vivo, tissue specimens from superficial epithelial bladder cancers were collected before and after IFN-α2b treatment, stained and analysed.

Twelve patients having superficial epithelial bladder cancer were evaluated for operation from one to three weeks prior to the actual operation. In connection to the evaluation visit biopsies were taken from normal area of the bladder and from the tumor. The patients were given 50 million units of IFN-α2b (IntronA, Schering-Plough) instilled to the bladder one-day prior to the operation. The cystectomy was performed and the patients underwent conventional ureteroenterocutaneostomy, enterocystoplasty or ureteroenteroumbilicostomy as the reconstructive operation. Three patients did not receive IFN-α prior to operation. Two of them received 100 mg epirubicin (Pharmorubicin, Pharmacia) instilled to the bladder one-day prior to the operation and one did not receive anything. Their tumors were analyzed before (biopsy) and after the operation and used as controls. All patients were Caucasian males. Patient characteristics appear in Table 2.

The bladder sample specimens were snap-frozen in liquid nitrogen and cut into 5 μm sections. Subsequently, sections were stained with anti-CD73 mAb 4G4 or 3G6 (negative control) as primary antibodies and peroxidase-conjugated rabbit anti-mouse IgG (DAKO A/S, Glostrup, Denmark) was used as a second stage antibody. The reaction was developed by adding 3,3'-diaminobenzidine tetrahydrochloride (Polysciences, Inc., Warrington, Pa.) in PBS. All incubations were 20 min with saturating mAb concentrations followed by two washes with PBS. The number of positive vessels/microscopic field (×200) was counted and intensity of the staining was semi-quantitatively evaluated. A combined score from 0 to 3 was given to each sample. Score 0 was assigned to samples with no positive blood vessels and score 3 to samples with staining equal to inflamed tonsil. Scores 1 and 2 were adjusted to cover the staining patterns in between. All samples were read blindly.

TABLE 2

Patient characteristics of IFN-α treated patients

| Patient number | Age (years) | Interval between biopsies and cystectomy | Histology (WHO grade) |
| --- | --- | --- | --- |
| 1 | 59 | 1 week | UC[A] grade 2 eosinohilic cystiris |
| 2 | 73 | 1 week | UC grade 3 |
| 3 | 64 | 1 week | UC grade 2 |
| 4 | 66 | 3 weeks | UC grade 3 |
| 5 | 70 | 1 week | SCC[B] grade 2 |
| 6 | 59 | 1 week | UC grade 3 with squamocellular component |
| 7 | 68 | 2 weeks | UC grade 3 |
| 8 | 65 | 3 weeks | UC grade 2 |
| 9 | 70 | 1 week | UC grade 1, invasive |

UC[A] = Urothelial cancer
SCC[B] = Squamous cell cancer

Figure 5:
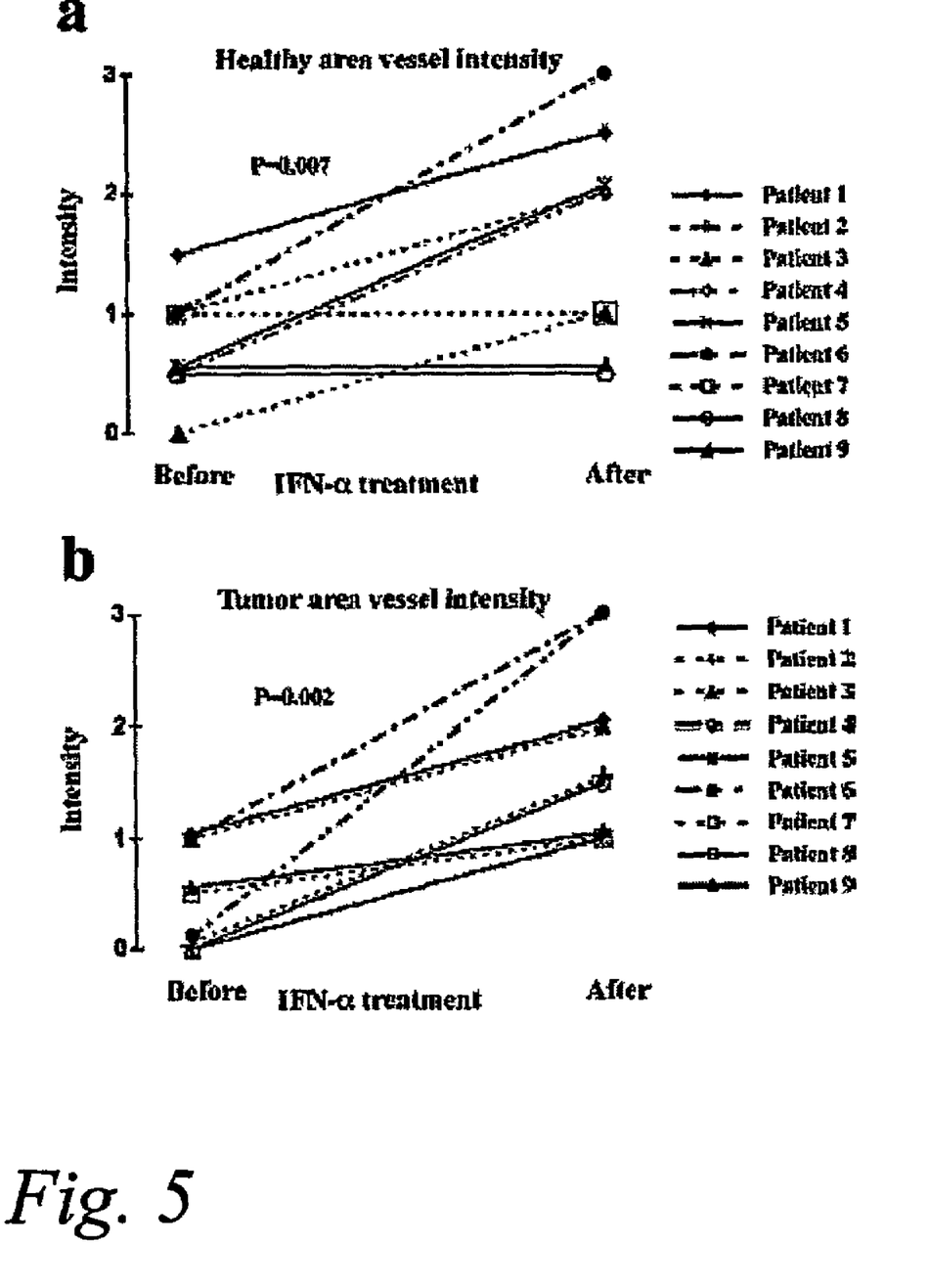
FIG. 5 is a summary of semiquantitative analysis of immunohistochemical stainings of urine bladder samples from (Panel a) healthy and Panel b) tumour areas before and after IFN treatment is presented.
Figure 6:
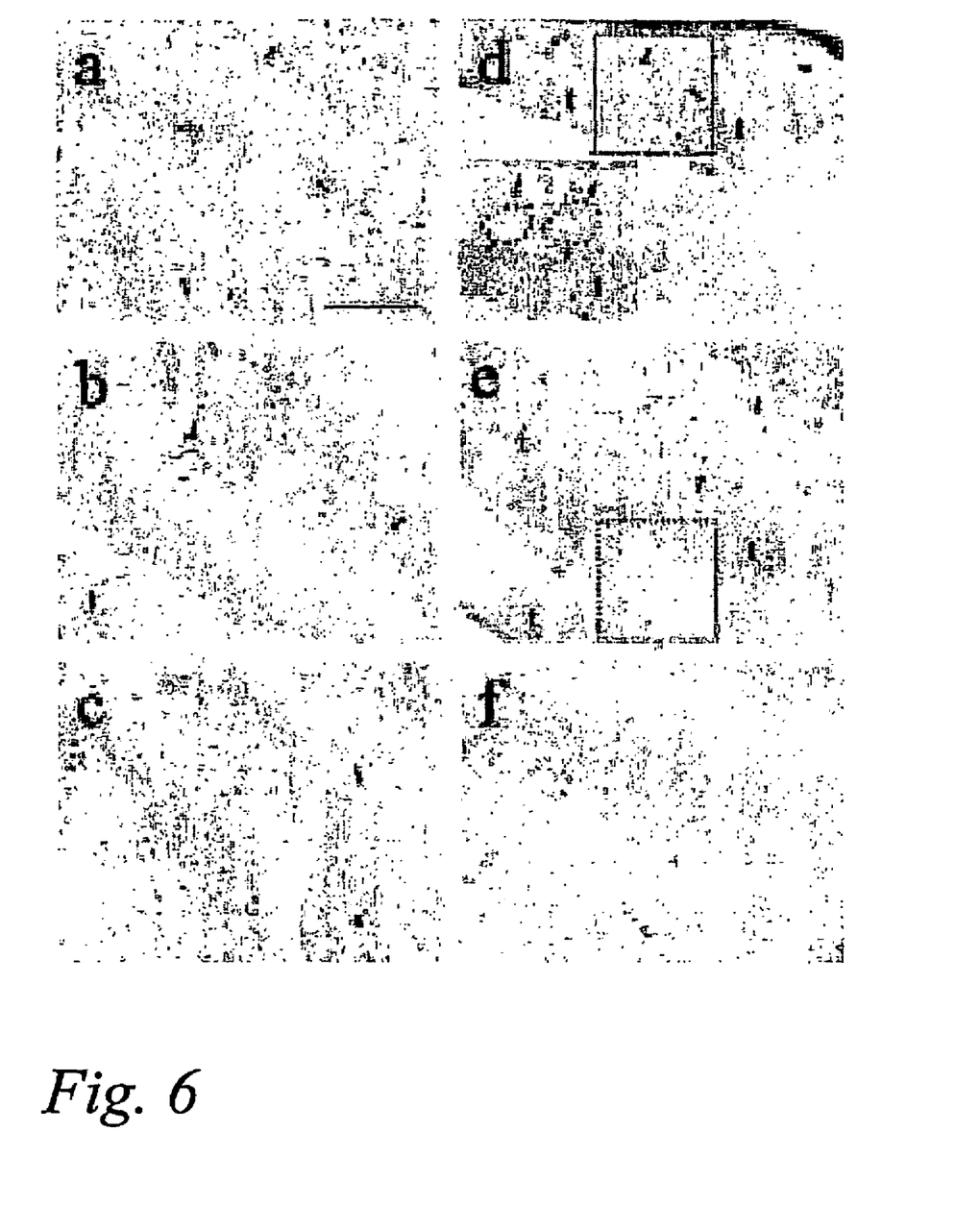

In two tumours the malignant cells were CD73 positive reflecting the fact that also some epithelial cells are CD73 positive. IFN-α produced a clear up-regulation of CD73 in vascular endothelium in both control and cancer vessels in vivo when compared to expression levels before and after treatment in control specimens (FIG. 5). However, no CD73 up-regulation was detected among the few normal lymphocytes present within the tumours. Similarly, the expression level of tumor cells remained constant during IFN-α2b treatment in those tumors which were positive for CD73 (FIG. 6). Three patients, who did not receive IFN-α and were used to control the possible up-regulation of CD73 caused by the biopsy and operation itself, did not show any significant increase in their CD73 expression (one patient did not show any change and two patients had an increase of 0.5 in endothelial CD73 expression within the tumor tissue). Thus the mean change of the control patients was 0.3 and that of treated patients 1.3 (P=0.02).

This experiment clearly shows that CD73 is upregulated in human subjects as a result of IFN-α administration in clinically feasible amounts.

EXAMPLE 6

Effect of IFN-α on Ecto-5'-Nucleotidase Activity

To determine whether IFN-α-induced increase of CD73 expression on HUVEC is accompanied by concomitant induction in ecto-5'-nucleotidase activity, a radiochemical assay for direct measurement of [$^3$H]AMP conversion into [$^3$H]adenosine was applied. Pre-treatment of HUVEC monolayers with IFN-α (1000 U/ml for 48 hours) caused significant increase in the rate of [$^3$H]AMP hydrolysis (FIG. 7a), whereas no significant activation of the enzyme activity was detected after PBL treatment with IFN-α (FIG. 7b).

Figure 7:
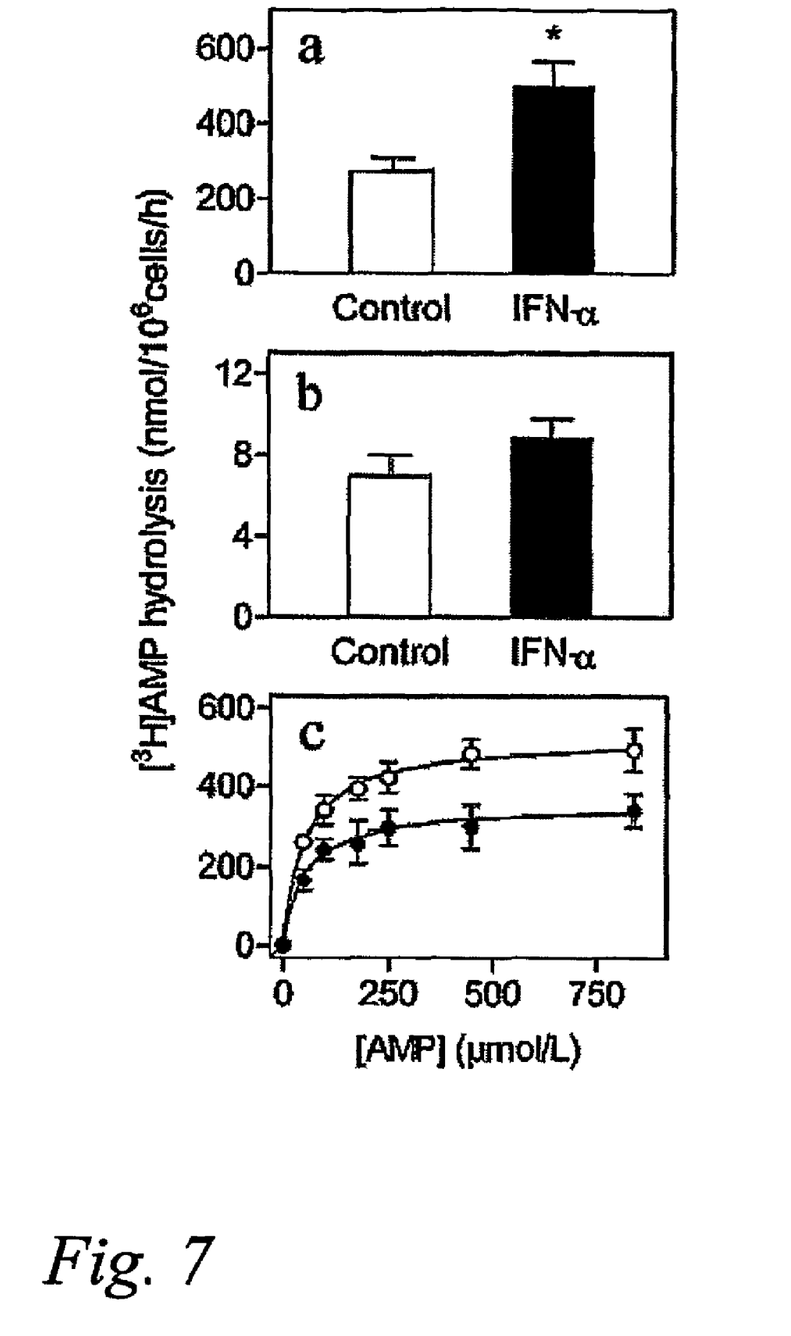

To further elucidate the mechanism of ecto-5'-nucleotidase activation, kinetic analysis of [$^3$H]AMP hydrolysis by control and IFN-treated HUVEC was carried out and these saturating curves can be seen in FIG. 7c. Statistical analysis revealed that IFN-α significantly increased the maximum hydrolysis rate ($V_{max}$) of 5'-nucleotidase as compared to non-treated cells (525±30 vs. 350±29 nmol/$10^6$ cells/hour) without any modification of the enzyme affinity (Km~50–60 µmol/L). These data suggest that IFN-α increases the number of enzymatically active 5'-nucleotidase molecules on the endothelial surface rather than induces conformational changes of the enzyme catalytic site.

Interestingly, use of the same approach with other nucleotide [$^3$H]ATP did not reveal significant changes of ATP-hydrolysing activities after HUVEC treatment with IFN-α (data not shown) confirming the specificity of ecto-5'-nucleotidase induction. To ensure that CD73 is not continuously secreted from lymphocytes into cell culture supernatant producing increased enzyme activity, [$^3$H]AMP conversion into [$^3$H]adenosine in cell culture media from IFN-α induced lymphocytes and non-treated control cells was analyzed. No significant change in enzymatic activity of cell culture media was found between control and IFN-α treatment (data not shown).

These experiments show that interferon-a increases ecto-5'-nucleotidase activity on endothelial cells.

EXAMPLE 7

Effect of IFN-α on HUVEC Membrane Function

Figure 8:
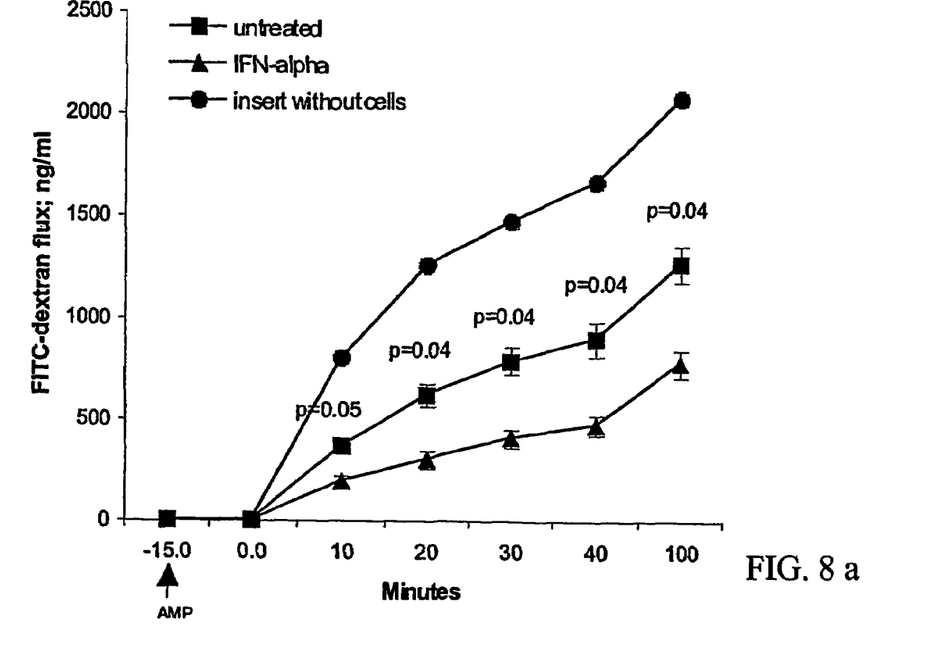

To study whether IFN-α upregulated CD73 expression and CD73 mediated increase in adenosine production is able to regulate HUVEC membrane function, the flux of FITC-labelled dextran through confluent endothelial monolayers growing on permeable insert wells was measured. At all time points examined, there was a significant difference (P<0.05) in the permeabilities of HUVEC treated with IFN-α (100 U/ml) for 3 days compared with untreated HUVEC as indicated by decreased flux of FITC-dextran (FIG. 8a). Pretreatment of HUVEC monolayers with a specific CD73 enzyme inhibitor, AMPCP reversed the permeability decrease associated with IFN-α treatment as demonstrated by increased flux of FITC-dextran (FIG. 8b).

These results confirm that IFN-α increases HUVEC membrane function in the presence of AMP. It strongly suggests that by increasing the expression of CD73 and thus the adenosine level vascular permeability decreases leading to diminished extravasation of inflammatory cells into the tissues.

Interferons produce a time and dose-dependent long-term upregulation of CD73 on endothelial cells but not on lymphocytes both at protein and RNA levels. Moreover, CD73 mediated production of adenosine is increased after IFN-α treatment on endothelial cells resulting in a decrease in the permeability of these cells.

EXAMPLE 8

Combined Treatment of Rats with AMP and IFN-beta in Multi-organ Failure

Model: The multiorgan failure was induced to rats (weight: 250 g) by clamping the mesenteric artery for 30 minutes. Thereafter, the reperfusion time was two hours. The rats in the treatment group were injected sybcutaneously with 10 000 units of IFN-beta 18-20 hours before the clamping of the artery. Throughout the actual experiment the animals received 37.5 mg AMP in 3 ml saline as a continuous intravenous infusion. Rats with induced multiorgan failure but without treatment served as controls. At the end of the experiment, the histology of the lungs, which is one of the major target organs in this experimental model was analyzed.

Figure 11:
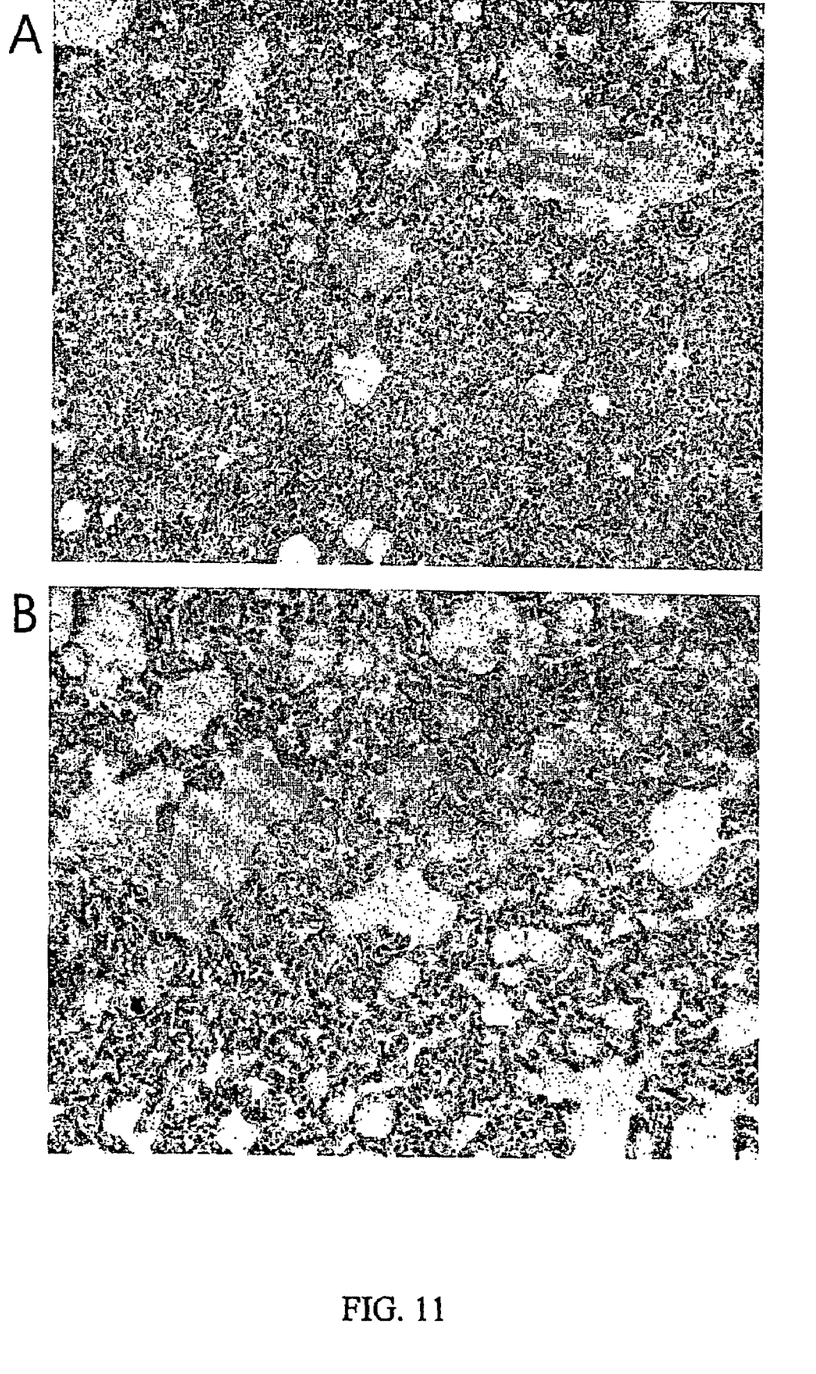
FIG. 11 shows Hematoxylin-eosin stainings of formalin-fixed paraffin-embedded sections of lungs of the rats with multiorgan failure without treatment (A) or with IFN-beta and AMP treatment (B).

Results: Lungs of the control rats without treatment showed collapsed alveolar space as can bee seen in FIG. 11 (A), whereas rats which received IFN-beta and AMP did not show marked collapsing of the alveolar space (B). Thus, treatment with IFN-beta and AMP protects from the complications of multiorgan failure.

Overall these results suggest that cytokines, and especially interferons are relevant in vivo regulators of CD73 in the endothelial-leukocyte microenvironment and thus have a fundamental role in controlling the extent of inflammation via CD73-dependent adenosine production.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

1. Thompson, L. F., Ruedi, J. M., Glass, A., Moldenhauer, G., Moller, P., Low, M. G., Klemens, M. R., Massaia, M., and Lucas, A. H. 1990. Production and characterization of monoclonal antibodies to the glycosyl phosphatidylinositol-anchored lymphocyte differentiation antigen ecto-5'-nucleotidase (CD73). Tissue Antigens 35:9-19.
2. Bouma, M. G., Jeunhomme, T. M. M. A., Boyle, D. L., Dentener, M. A., Voitenok, N. N., van den Wildenberg, F. A. J. M., and Buurman, W. A. 1997. Adenosine inhibits neutrophil degranulation in activated human whole blood: involvement of adenosine A2 and A3 receptors. J. Immunol. 158:5400-5408.
3. Olah, M. E., and Stiles, G. L. 1995. Adenosine receptor subtypes: characterization and therapeutic regulation. Annu. Rev. Pharmacol. Toxicol. 35:581-606.
4. Heurteaux, C., Lauritzen, I., Widmann, C., and Lazdunski, M. 1995. Essential role of adenosine, adenosine A1 receptors, and ATP-sensitive K+ channels in cerebral ischemic preconditioning. Proc. Natl. Acad. Sci. USA 92:4666-4670.
5. Linden, J. 2001. Molecular approach to adenosine receptors: receptor-mediated mechanisms of tissue protection. Annu. Rev. Pharmacol. Toxicol. 41:775-787.

The invention claimed is:

1. A method of controlling the extent of inflammation in an individual in vivo via CD73-dependent adenosine production, which comprises administering to said individual (1) a cytokine selected from the group consisting of interferon alpha, interferon beta and interferon gamma in an amount effective to induce endothelial CD73 expression and (2) an agent in an amount effective for maintaining adenosine levels in said individual, wherein said agent is selected from the group consisting of (i) adenosine monophosphate (AMP), (ii) an adenylate kinase inhibitor which prevents AMP from conversion into adenosine diphosphate (ADP) or adenosine triphosphate (ATP) and (iii) an adenosine deaminase inhibitor which prevents the decomposition of adenosine.

2. The method according to claim 1, wherein the inflammation results from (a) tissue trauma, (b) a reperfusion injury resulting from myocardial infarction or stroke, (c) a reperfusion injury resulting from organ transplantation or a surgical operation, (d) cancer or cancer metastasis, or (e) an allergic condition.

3. The method according to claim 1, wherein the cytokine is interferon alpha.

4. The method according to claim 1, wherein the cytokine is interferon beta.

5. The method according to claim 1, wherein the cytokine is interferon gamma.

6. The method according to claim 1, wherein the agent is adenosine monophosphate.

7. The method according to claim 1, wherein the agent is an adenylate kinase inhibitor.

8. The method according to claim 1, wherein the agent is an adenosine deaminase inhibitor.

9. The method according to claim 2, wherein the inflammation results from (a) tissue trauma, (b) a reperfusion injury resulting from myocardial infarction or stroke, or (c) cancer or cancer metastasis and the administration of the cytokine is started immediately when the patient is brought to care.

10. The method according to claim 2, wherein the inflammation results from a reperfusion injury resulting from organ transplantation or a surgical operation and the administration of the cytokine is staffed before the organ transplantation or the surgical operation.

* * * * *

SEQUENCE LISTING

<160> NUMBER OF SEQ ID NOS: 3

<210> SEQ ID NO 1
<211> LENGTH: 21
<212> TYPE: DNA
<213> ORGANISM: Homo sapiens

<400> SEQUENCE: 1
ctgggagctt acgattttgc a                                      21

<210> SEQ ID NO 2
<211> LENGTH: 18
<212> TYPE: DNA
<213> ORGANISM: Homo sapiens

<400> SEQUENCE: 2
cctcgctggt ctgctcca                                          18

<210> SEQ ID NO 3
<211> LENGTH: 20
<212> TYPE: DNA
<213> ORGANISM: Homo sapiens

<400> SEQUENCE: 3
ccaacgacgt gcacagccgg                                        20